(12) United States Patent
Besser et al.

(10) Patent No.: US 6,814,956 B2
(45) Date of Patent: Nov. 9, 2004

(54) NON-FLAMMABLE AEROSOL INSECTICIDAL COMPOSITIONS

(75) Inventors: Brice Besser, Maple Grove, MN (US); Richard Merwin, Long Lake, MN (US)

(73) Assignee: McLaughlin Gormley King Company, Minneapolis, MN (US)

(*) Notice: Subject to any disclaimer, the term of this patent is extended or adjusted under 35 U.S.C. 154(b) by 0 days.

(21) Appl. No.: 10/155,606

(22) Filed: May 23, 2002

(65) Prior Publication Data

US 2003/0220296 A1 Nov. 27, 2003

(51) Int. Cl.⁷ .......................... A01N 25/06; A01N 65/00
(52) U.S. Cl. ................. 424/45; 424/405; 424/DIG. 10; 514/65; 514/67; 514/70; 514/531
(58) Field of Search .................. 424/DIG. 10, 405, 424/45, 44, 47; 514/521, 531, 421, 468, 65, 67, 70

(56) References Cited

U.S. PATENT DOCUMENTS

| | | | | |
|---|---|---|---|---|
| 4,595,522 A | * | 6/1986 | Bartlett et al. | 252/305 |
| 4,904,464 A | * | 2/1990 | Albanese | 424/45 |
| 5,064,639 A | * | 11/1991 | Dohara et al. | 424/45 |
| 5,773,016 A | * | 6/1998 | Nelson | 424/405 |
| 6,333,022 B1 | * | 12/2001 | Tanaka | 424/45 |

FOREIGN PATENT DOCUMENTS

GB  2886405  * 8/1995

OTHER PUBLICATIONS

ASTM D–3065–94,"Standard Test Methods for Flammability of Aerosol Products," American Society for Testing and Materials, West Conshohocken, PA, 1995.
40 C.F.R. § 156.10, revised as of Jul. 1, 2000 (12 pages).
Material Safety Data Sheet for PYROCIDE® Flusher 51922, McLaughlin Gormley King Co., Minneapolis, MN, Dec. 2001 (8 pages).

* cited by examiner

*Primary Examiner*—Neil S. Levy
(74) *Attorney, Agent, or Firm*—Popovich, Wiles & O'Connell, P.A.

(57) ABSTRACT

A non-flammable aerosol composition insectidal composition comprising 0.01 to 20 weight percent of one or more insecticides; 5 to 25 weight percent of one or more compounds selected from the group consisting of acetone, methyl ethyl ketone, and $C_1$- to $C_8$-alcohol; 5 to 30 weight percent of one or more compounds selected from the group consisting of hydrocarbon propellants, dimethyl ether, and 1,1-difluoroethane; and 60 to 90 weight percent of one or more non-combustible hydrofluorocarbons.

20 Claims, 1 Drawing Sheet

Acetone

NON-FLAMMABLE AEROSOL INSECTICIDAL COMPOSITIONS

FIELD OF THE INVENTION

This invention relates to non-flammable aerosol insecticidal compositions.

BACKGROUND OF THE INVENTION

Pyrethrins refer to a group of closely related esters extracted from the Pyrethrum flower (*chrysanthemum cinerariaefolium*). These compounds are known to be effective pesticides. Pyrethrins tend to have a relatively low degree of toxicity to humans and animals and hence are desirable to use for pest control. Aerosol formulations containing pyrethrins have the added desirability of effectively delivering small amounts of insecticide due to the dispersion of active ingredient and penetrating nature of an aerosol spray.

However, a potential issue with aerosols is flammability of the spray, generally due to the flammability of solvents and/or propellants used in the formulation. During inspection or treatment the applicator may spray in areas harboring insect population that often are in locations where potential ignition sources exist, e.g., pilot lights around stoves, hot water heaters, etc. Because of these sensitive applications, a need exists for an aerosol formulation that is not flammable.

SUMMARY OF THE INVENTION

The invention provides a non-flammable aerosol composition insectidal composition comprising: (i) 0.01 to 20 weight percent of one or more insecticides; (ii) 5 to 25 weight percent of one or more compounds selected from the group consisting of acetone, methyl ethyl ketone, and $C_1$- to $C_8$-alcohol; (iii) 5 to 30 weight percent of one or more compounds selected from the group consisting of hydrocarbon propellants, dimethyl ether, and 1,1-difluoroethane; and (iv) 60 to 90 weight percent of one or more non-combustible hydrofluorocarbons.

It is to be understood that both the foregoing general description and the following detailed description are exemplary and explanatory and are intended to provide further explanation of the invention as claimed.

DETAILED DESCRIPTION OF THE PREFERRED EMBODIMENTS

Figure 1:
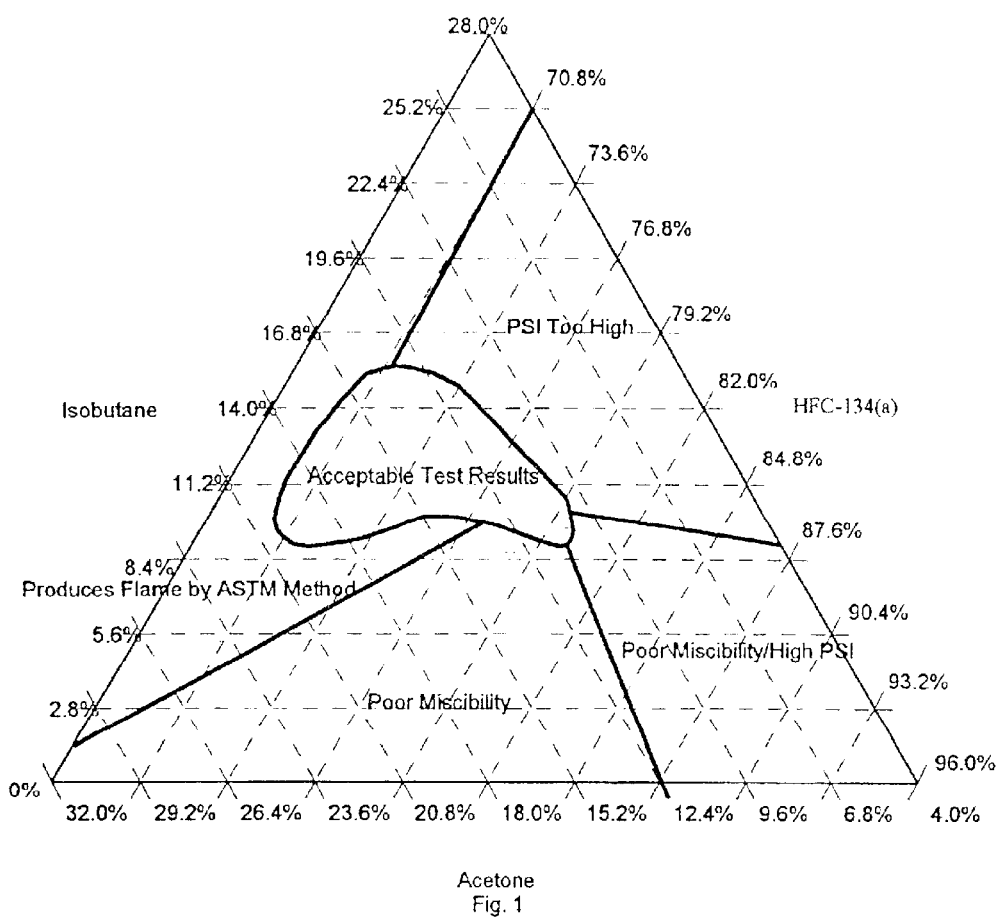
FIG. 1 is a tertiary phase diagram showing the concentrations of acetone, isobutane, and 1,1,1,2-tetrafluoroethane (HFC-134a).

The invention provides a non-flammable aerosol composition insectidal composition comprising: (i) 0.01 to 20 weight percent of one or more insecticides; (ii) 5 to 25 weight percent of one or more compounds selected from the group consisting of acetone, methyl ethyl ketone, and $C_1$- to $C_8$-alcohol; (iii) 5 to 30 weight percent of one or more compounds selected from the group consisting of hydrocarbon propellants, dimethyl ether, and 1,1-difluoroethane; and (iv) 60 to 90 weight percent of one or more non-combustible hydrofluorocarbons. In a preferred embodiment, the composition comprises: (i) 0.01 to 20 weight percent of one or more insecticides; (ii) 5 to 25 weight percent acetone; (iii) 5 to 30 weight percent of one or more compounds selected from the group consisting of hydrocarbon propellants, dimethyl ether, and 1,1-difluoroethane; and (iv) 60 to 90 weight percent of one or more non-combustible hydrofluorocarbons. In another preferred embodiment, the composition comprises: (i) 1 to 10 weight percent of one or more insecticides; (ii) 5 to 20 weight percent acetone; (iii) 5 to 20 weight percent of one or more compounds selected from the group consisting of hydrocarbon propellants, dimethyl ether, and 1,1-difluoroethane; and (iv) 65 to 85 weight percent of one or more non-combustible hydrofluorocarbons.

The composition preferably comprises one or more insecticides selected from the group consisting of knockdown agents, toxicants, synergists, and insect growth regulators. In another embodiment, the composition preferably comprises one or more insecticides selected from the group consisting of pyrethrins, prallethrin, imipothrin, d-trans allethrin, esbiol, esbiothrin, tetramethrin, pynamin forte, permethrin, cypermethrin, lambda-cyhalothrin, cyfluthrin, d-phenothrin, esfenvalerate, bifenthrin, piperonyl butoxide, n-octyl bicycloheptene dicarboximide, pyriproxyfen, methoprene, and isomers thereof. In preferred embodiments, the composition comprises: (i) pyrethrins; (ii) pyrethrins and piperonyl butoxide; or (iii) pyrethrins, piperonyl butoxide, and n-octyl bicycloheptene dicarboximide (MGK® 264).

The composition preferably comprises 1,1,1,2-tetrafluoroethane. The composition preferably comprises pyrethrins, piperonyl butoxide, n-octyl bicycloheptene dicarboximide, and 1,1,1,2-tetrafluoroethane.

The composition preferably comprises one or more hydrocarbon propellants selected from the group consisting of acetylene, methane, ethane, ethylene, propane, propene, n-butane, isobutane, isobutene, pentane, pentene, isopentane, and isopentene. The composition preferably comprises one or more hydrocarbon propellants selected from the group consisting of isobutane, propane, and n-butane. The composition preferably comprises isobutane.

The invention provides a non-flammable aerosol insecticidal composition comprising: (i) 0.1 to 5 weight percent pyrethrins; (ii) 0.1 to 10 weight percent of one or more synergists; (iii) 7 to 20 weight percent acetone; (iv) 7 to 15 weight percent isobutane; and (v) 60 to 80 weight percent 1,1,1,2-tetrafluoroethane. The invention also provides a non-flammable aerosol insecticidal composition comprising: (i) 0.1 to 1 weight percent pyrethrins; (ii) 0.5 to 2 weight percent piperonyl butoxide; (iii) 1 to 2 weight percent n-octyl bicycloheptene dicarboximide; (iv) 10 to 20 weight percent acetone; (v) 8 to 14 weight percent isobutane; and (vi) 70 to 80 weight percent 1,1,1,2-tetrafluoroethane.

In a preferred embodiment, when the composition is exposed to a flame extension test in accordance with American Society for Testing and Materials (ASTM) D-3065-94, Sec. 4–7, the flame extension is less than 18 inches.

The composition preferably does not comprise water.

This invention provides a non-flammable aerosol composition comprising an active ingredient, solvent, and propellants. The propellant preferably comprises a mixture of a hydrocarbon propellant such as isobutane and a non-combustible hydrofluorocarbon such as 1,1,1,2-tetrafluoroethane ($CF_3CH_2F$) (HFC134A), which has been discovered to produce a non-flammable composition when used with predetermined amounts of solvent in an aerosol spray. Active ingredients include those useful for pest control, i.e., insecticides such as knockdown agents, biological control agents, insect growth regulators, and repellents.

In a preferred embodiment, this invention comprises an insecticide dissolved in a solvent and pressurized with propellants in a ratio that produces a non-flammable spray. The composition may also contain synergists, toxicants, and insect growth regulators.

Insecticides suitable for use in this invention include pyrethrins, prallethrin, imiprothrin, d-trans allethrin, esbiol, esbiothrin, tetramethrin, and pynamin forte. A preferred insecticide for use in this invention is the toxicant pyrethrins in combination with the dual synergists, piperonyl butoxide and n-octyl bicycloheptene dicarboximide. This insecticide is available from McLaughlin Gormley King Company, Minneapolis, Minn., as PYROCIDE® Intermediate 5192.

Preferred embodiments of the formulation include one or more synergists. These are compounds that act to make the insecticide more effective at lower concentrations, and include piperonyl butoxide and N-octyl bicycloheptene dicarboximide.

In addition, toxicants may be present, and these include permethrin, cypermethrin, lambda-cyhalothrin, cyfluthrin, d-phenothrin, esfenvalerate and bifenthrin, and isomers thereof.

Insect growth regulators (IGR's) may also be present, and such include pyriproxyfen (NYLAR®) and methoprene.

The insecticide and any other desired ingredients are mixed with and solubilized by a hydrocarbon carrier or solvent. Preferably, the insecticide is miscible or completely homogeneous with no phase separation. Phase separation can be observed by transferring the aerosol contents to a glass aerosol container. Suitable carriers or solvents include ketones, alcohols, esters, and ethers, petroleum distillates (comprising normal, iso & cyclo paraffin blends), or chlorinated solvents and/or mixtures of these. A preferred solvent is acetone.

A propellant is mixed with and used to deliver the active material and solvent by spraying. The propellant blend of this invention is non-flammable, and preferably includes two components mixed in accordance with the phase diagram shown in FIG. 1. The first component is isobutane and the second is 1,1,1,2-tetrafluoroethane.

Suitable hydrocarbon propellants include acetylene, methane, ethane, ethylene, propane, propene, n-butane, n-butene, isobutane, isobutene, pentane, pentene, isopentane and isopentene, dimethyl ether, and 1,1 difluoroethane and mixtures thereof. Preferred hydrocarbon propellants include propane, n-butane, isobutane, pentane and isopentane, and the most preferred is isobutane. A suitable non-flammable component propellant is 1,1,1,2-tetrafluoroethane (HFC-134a). These propellants are preferably combined in weight ratios ranging from 0.1:1 to 0.25:1 of hydrocarbon propellant to non-flammable propellant. Example 1 below is 0.15 to 1 isobutane to HFC-134a.

The propellant mixture is combined with the solution of active ingredient and placed into a container. The proportion of solvent (containing the active ingredient) to propellant ranges from 0.1:1 to 0.5:1.

The compositions of this invention are prepared by mixing the insecticide, petroleum distillate, and any other desired additives in acetone to dissolve and disperse them. The required amount of the product is then added to the appropriate aerosol container and then the units are crimped and pressurized with the designed propellant.

The pressure in a sealed container is of course determined by all of its contents, but both organic solvents and propellants tend to be particularly volatile, thus increasing the pressure in a closed system. The pressure in the container will have a determining effect on spray rates. To get the desired spray rate, the pressure typically ranges from 40 psig to 70 psig. The pressure in the container should remain below 180 psig when warmed to 130° F., as required by the U.S. Department of Transportation (DOT). The DOT has established certain acceptable ranges for finished aerosol packages depending on the design strength of the can. Currently ratings are given for steel cans as follows: 2N for cans capable of withstanding 140 psig at 130° F.; 2P for cans capable of withstanding 160 psig max; and 2Q for cans capable of withstanding 180 psig. If higher psig results, damage, if not catastrophic failure, to the container, may result. If the pressure exceeds the can strength, doming of the top and/or bottom of the aerosol container is observed. For example, increasing pressure beyond the structural integrity of the container causes bulging of the container.

The non-flammable insecticidal aerosol of this invention is particularly useful for various pest control applications, such as crawling and flying insects, total release aerosols, and intermittent devices. Total release aerosols are designed with a special valve and actuator system that when tripped will lock and will release all of its contents. This is used when it is desired to treat a whole room and limit the potential exposure of the applicator. Intermittent devices or metered aerosols are used in restaurants or where food is handled to control flies and cockroaches. They are packaged in a device that has a timer mechanism that will disperse a small amount of insecticide at predetermined intervals.

Test Methods

Flammability

To test the flammability of a mixture, the mixture is placed into a container and the units are then crimped and pressurized. The units are crimped and pressurized at room temperature via pressure filling (thru the valve) or undercapped. The contents of the container are then sprayed at a flame and the length of the flame (if any) is measured. This test is done in accordance with ASTM D-3065-94, Sec. 4–7, wherein a flame source such as a candle is mounted on a holder. The aerosol test unit is conditioned to 70° F. +/−1°. A measuring device is aligned so that its zero point is in line with the flame. The pressurized container holding the material to be tested is held six inches away and sprayed toward the flame. While discharging the unit, the spray is positioned so that it sprays through the top third of the flame. The length of a flame produced if the container's contents are ignited is measured and recorded. This is replicated three times and the average of the three is reported. It is convenient, and somewhat safer, to photograph this test and examine the flame test results in this manner.

Per EPA's Code of Federal Regulation 40, Part 156.10, an aerosol is to be labeled as non-flammable and pass the flame test if the flame extension is recorded to be less than 18 inches. It is preferred that compositions of the invention not produce any flame, but in fact will extinguish the flame per ASTM D-3065-94, Sec 4–7 methodology.

Pressure

Various mixtures were placed into containers and tested to determine the pressure rise when the filled container was subjected to a hot water bath. Mixtures which "passed" this test had a pressure of less than 180 psi when warmed to and held at 130° F. for 30 to 40 minutes.

The test was conducted by warming the filled aerosol test container by fully immersing it in a water bath that has been set at 130° F. The can is to be held at this temperature until temperature equilibrium is achieved (typically 30 to 40 minutes depending on the size of the can). Pressure is measured using a pressure gauge and inspection of the can integrity is done by observing for blemishes, typical signs are doming at the top or bottom of the can.

EXAMPLES

The following materials and procedures were used for all examples:

PYROCIDE® Intermediate 5192 (commercially available from McLaughlin Gormley King Company, Minneapolis, Minn. comprising 9.0 weight percent pyrethrins (CAS# 8003-34-7), 18.0 weight percent piperonyl butoxide (butylcarbityl)(6-propylpiperonyl ether) (CAS# 51-03-6), 30.0 weight percent N-octyl bicycloheptene dicarboximide (CAS# 113-48-4) and petroleum distillate (CAS# 64742-47-8) was mixed with acetone (CAS# 67-64-1) and stirred to obtain complete uniformity. The correct amount of the solution was added to a 17 oz. 2Q aerosol container, crimped, and pressurized with the correct blend of isobutane (CAS# 68476-86-8) and 1,1,1,2-tetrafluoroethane (HFC-134a) (CAS# 811-97-2). In each example below, 26.7 g of Pyrocide® Intermediate 5192 was added to a 17 oz. 2Q can.

The following examples show the amounts of each component in a formulation and the results of testing.

Example 1

| Component | Percent by weight |
|---|---|
| PYROCIDE 5192 | 5.55 |
| Acetone | 5.55 |
| Isobutane | 18.00 |
| HFC-134a | 70.90 |

This mixture of components was miscible and passed the flame test when sprayed as an aerosol. The filled 2Q can domed, when warmed to 130° F.

Example 2

| Component | Percent by weight |
|---|---|
| PYROCIDE 5192 | 5.55 |
| Acetone | 14.55 |
| Isobutane | 9.0 |
| HFC-134a | 70.90 |

This mixture of components was miscible. A seven-inch flame was observed during the flame extension test. It passed the pressure test.

Example 3

| Component | Percent by weight |
|---|---|
| PYROCIDE 5192 | 5.55 |
| Acetone | 10.00 |
| Isobutane | 13.55 |
| HFC-134a | 70.90 |

This mixture of components was miscible and passed the flame test when sprayed as an aerosol. The filled 2Q can domed, when warmed to 130° F.

Example 4

| Component | Percent by weight |
|---|---|
| PYROCIDE 5192 | 5.55 |
| Acetone | 5.55 |
| Isobutane | 14.00 |
| HFC-134a | 74.90 |

This mixture of components was miscible and passed the flame test when sprayed as an aerosol. The filled 2Q can domed, when warmed to 130° F.

Example 5

| Component | Percent by weight |
|---|---|
| PYROCIDE 5192 | 5.55 |
| Acetone | 18.90 |
| Isobutane | 4.75 |
| HFC-134a | 70.80 |

This mixture of components was miscible and passed the flame test when sprayed as an aerosol. The filled 2Q can domed, when warmed to 130° F.

Example 6

| Component | Percent by weight |
|---|---|
| PYROCIDE 5192 | 5.55 |
| Acetone | 18.90 |
| Isobutane | 18.90 |
| HFC-134a | 56.70 |

This mixture of components was miscible and passed the pressure test. It produced a flame during the flame extension evaluation.

Example 7

| Component | Percent by weight |
|---|---|
| PYROCIDE 5192 | 5.55 |
| Acetone | 4.75 |
| Isobutane | 4.70 |
| HFC-134a | 85.00 |

This mixture of components produced a phase separation. It passed the flame test when sprayed as an aerosol. The filled 2Q can domed when warmed to 130° F.

Example 8

| Component | Percent by weight |
| --- | --- |
| PYROCIDE 5192 | 5.55 |
| Acetone | 4.75 |
| Isobutane | 18.90 |
| HFC-134a | 70.80 |

This mixture of components was produced a phase separation. It passed the flame test when sprayed as an aerosol. The filled 2Q can domed, when warmed to 130° F.

Example 9

| Component | Percent by weight |
| --- | --- |
| PYROCIDE 5192 | 5.55 |
| Acetone | 12.50 |
| Isobutane | 11.05 |
| HFC-134a | 70.90 |

This mixture of components was miscible and passed the flame test when sprayed as an aerosol. The filled can exhibited no bulging and passed the pressure test.

Example 10

| Component | Percent by weight |
| --- | --- |
| PYROCIDE 5192 | 5.55 |
| Acetone | 14.00 |
| Isobutane | — |
| HFC-134a | 80.45 |

This mixture of components produced a phase separation. Passed the flame test when sprayed as an aerosol. Passed the pressure test.

Example 11

| Component | Percent by weight |
| --- | --- |
| PYROCIDE 5192 | 5.55 |
| Acetone | — |
| Isobutane | — |
| HFC-134a | 94.45 |

This mixture of components was not miscible. It passed the flame test when sprayed as an aerosol. The filled 2Q can domed, when warmed to 130° F.

The most preferred aerosol mixtures contain about 0.01 to 9.0% insecticide, 1.0 to 30% petroleum distillate, 10 to 19% acetone, 9 to 14% isobutane, and 65 to 80% HFC-134a. The most preferred embodiment is a mixture that is completely miscible (no phase separation), produces no flame in the flame extension test, and does not exceed a pressure of 180 psi in the pressure test.

The above description is provided for the purpose of describing embodiments of the invention and is not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A non-flammable aerosol insecticidal composition comprising:
 (i) 0.01 to 20 weight percent of a mixture of insecticides comprising pyrethrins, piperonyl butoxide, and n-octyl bicycloheptene dicarboximide;
 (ii) 5 to 25 weight percent of one or mare compounds selected from the group consisting of acetone, methyl ethyl ketone, and $C_1$- to $C_8$-alcohol;
 (iii) 5 to 30 weight percent of one or more compounds selected from the group consisting of hydrocarbon propellants, dimethyl ether, and 1,1-difluoroethane; and
 (iv) 60 to 90 weight percent of 1,1,1,2-tetrafluoroethane,
 wherein the weight percent is calculated as a percentage of the total composition, and
 wherein when the composition is exposed to a flame extension test in accordance with American Society for Testing and Materials (ASTM) D-3065-94, Sec. 4–7, the flame extension is less than 18 inches.

2. The non-flammable aerosol insecticidal composition of claim 1, wherein the composition comprises 5 to 25 weight percent of acetone.

3. The non-flammable aerosol insecticidal composition of claim 1, wherein the composition comprises one or more hydrocarbon propellants selected from the group consisting of acetylene, methane, ethane, ethylene, propane, propene, n-butane, isobutane, isobutene, pentane, pentene, isopentane, and isopentene.

4. The non-flammable aerosol insecticidal composition of claim 1, wherein the composition comprises one or more hydrocarbon propellants selected from the group consisting of isobutane, propane, and n-butane.

5. The non-flammable aerosol insecticidal composition of claim 1, wherein the composition comprises isobutane.

6. The non-flammable aerosol insecticidal composition of claim 1, wherein the composition does not comprise water.

7. The non-flammable aerosol insecticidal composition of claim 1, wherein the composition comprises;
 (i) 0.01 to 20 weight percent of a mixture of insecticides comprising pyrethrins, piperonyl butoxide, and n-octyl bicycloheptene dicarboximide;
 (ii) 5 to 25 weight percent of acetone;
 (iii) 5 to 30 weight percent of one or more compounds selected from the group consisting of hydrocarbon propellants, dimethyl ether, and 1,1-difluoroethane; and
 (iv) 60 to 90 weight percent of 1,1 1,2-tetrafluoroethane.

8. The non-flammable aerosol insecticidal composition of claim 7, wherein the composition comprises one or more hydrocarbon propellants selected from the group consisting of acetylene, methane, ethane, ethylene, propane, propene, n-butane, isobutane, isobutene, pentane, pentene, isopentane, and isopentene.

9. The non-flammable aerosol insecticidal composition of claim 7, wherein the composition comprises one or more hydrocarbon propellants selected from the group consisting of isobutane, propane, and n-butane.

10. The non-flammable aerosol insecticidal composition of claim 7, wherein the composition comprises isobutane.

11. The non-flammable aerosol insecticidal composition of claim 7, wherein the composition does not comprise water.

12. The non-flammable aerosol insecticidal composition of claim 1, wherein the composition comprises:
   (i) 1 to 10 weight percent of a mixture of insecticides comprising pyrethrins, piperonyl butoxide, and n-octyl bicycloheptene dicarboximide;
   (ii) 5 to 20 weight percent of acetone;
   (iii) 5 to 20 weight percent of one or more compounds selected from the group consisting of hydrocarbon propellants, dimethyl ether, and 1,1-difluoroethane; and
   (iv) 65 to 85 weight percent of 1,1,1,2-tetrafluoroethane.

13. The non-flammable aerosol insecticidal composition of claim 12, wherein the composition comprises one or more hydrocarbon propellants selected from the group consisting of acetylene, methane, ethane, ethylene, propane, propene, n-butane, isobutane, isobutene, pentane, pentene, isopentane, and isopentene.

14. The non-flammable aerosol insecticidal composition of claim 12, wherein the composition comprises one or more hydrocarbon propellants selected from the group consisting of isobutane, propane, and n-butane.

15. The non-flammable aerosol insecticidal composition of claim 12, wherein the composition comprises isobutane.

16. The non-flammable aerosol insecticidal composition of claim 12, wherein the composition does not comprise water.

17. A non-flammable aerosol insecticidal composition comprising:
   (i) 0.1 to 5 weight percent pyrethrins;
   (ii) 0.1 to 10 weight percent of one or more synergists;
   (iii) 7 to 20 weight percent acetone;
   (iv) 7 to 15 weight percent isobutane; and
   (v) 60 to 80 weight percent 1,1,1,2-tetrafluoroethane,
   wherein the weight percent is calculated as a percentage of the total composition, and
   wherein when the composition is exposed to a flame extension test in accordance with ASTM D-3065-94, Sec. 4–7, the flame extension is less than 18 inches.

18. The non-flammable aerosol insecticidal composition of claim 17, wherein the composition does not comprise water.

19. A non-flammable aerosol insecticidal composition comprising:
   (i) 0.1 to 1 weight percent pyrethrins;
   (ii) 0,5 to 2 weight percent piperonyl butoxide;
   (iii) 1 to 2 weight percent n-octyl bicycloheptene dicarboximide;
   (iv) 10 to 20 weight percent acetone;
   (v) 8 to 14 weight percent isobutane; and
   (vi) 70 to 80 weight percent 1,1,1,2-tetrafluoroethane,
   wherein the weight percent is calculated as a percentage of total composition, and
   wherein when the composition is exposed to a flame extension test in accordance with ASTM D-3065-94, Sec. 4–7, the flame extension is less than 18 inches.

20. The non-flammable aerosol insecticidal composition of claim 19, wherein the composition does not comprise water.

* * * * *